United States Patent

Halberstadt et al.

[11] Patent Number: 5,081,035
[45] Date of Patent: Jan. 14, 1992

[54] BIOREACTOR SYSTEM

[75] Inventors: Craig R. Halberstadt; A. Rees Midgley, both of Ann Arbor, Mich.

[73] Assignee: The University of Michigan, Ann Arbor, Mich.

[21] Appl. No.: 654,418

[22] Filed: Feb. 11, 1991

Related U.S. Application Data

[63] Continuation of Ser. No. 182,715, Apr. 18, 1988, abandoned.

[51] Int. Cl.$^5$ .................................. C12M 3/06
[52] U.S. Cl. .......................... 435/284; 435/240.242; 435/311; 435/313; 210/321.79
[58] Field of Search .................. 435/284–286, 435/288, 311, 313, 240.242; 210/321.73, 321.78, 321.77, 321.80, 500.23

[56] References Cited

U.S. PATENT DOCUMENTS

| | | | |
|---|---|---|---|
| 3,812,016 | 5/1974 | Muller | 435/285 |
| 3,821,087 | 6/1974 | Knazek et al. | 435/285 |
| 3,853,712 | 12/1974 | House et al. | 435/285 |
| 3,883,393 | 5/1975 | Knazek et al. | 435/284 |
| 3,925,165 | 12/1975 | Muller | 435/285 |
| 3,941,662 | 3/1976 | Munder et al. | 435/285 |
| 3,997,396 | 12/1976 | Delente | 435/285 |
| 4,178,209 | 12/1979 | Tolbert et al. | 435/286 |
| 4,184,922 | 1/1980 | Knazek et al. | 435/284 |
| 4,220,725 | 9/1980 | Knazek et al. | 435/285 |
| 4,228,242 | 10/1980 | Girard et al. | 435/284 |
| 4,242,459 | 12/1980 | Chick et al. | 435/283 |
| 4,246,120 | 1/1981 | Baudet et al. | 210/321.79 |
| 4,310,630 | 1/1982 | Girard et al. | 435/284 |
| 4,311,798 | 1/1982 | Katinger et al. | 435/286 |
| 4,391,912 | 7/1983 | Yoshida et al. | 435/284 |
| 4,440,853 | 4/1984 | Michaels et al. | 435/65 |
| 4,442,206 | 4/1984 | Michaels et al. | 435/171 |
| 4,537,860 | 8/1985 | Tolbert et al. | 435/240.242 X |
| 4,546,083 | 10/1985 | Meyers et al. | 435/284 X |
| 4,559,299 | 12/1985 | Rotman | 435/29 |
| 4,647,539 | 3/1987 | Bach | 435/284 |
| 4,649,114 | 3/1987 | Mittenburger et al. | 435/284 |
| 4,808,315 | 2/1989 | Manabe et al. | 210/645 |

FOREIGN PATENT DOCUMENTS

| | | | |
|---|---|---|---|
| 3809163 | 9/1988 | Fed. Rep. of Germany | 435/284 |
| 1025477 | 2/1986 | Japan | 435/284 |
| 8401959 | 5/1984 | PCT Int'l Appl. | 435/285 |

Primary Examiner—Robert J. Hill, Jr.
Assistant Examiner—William H. Belsner
Attorney, Agent, or Firm—Rohm & Monsanto

[57] ABSTRACT

A system for continuous perfusion culturing of anchorage-dependent and anchorage-independent mammalian cell lines, inter alia, wherein in vivo capillary bed conditions are simulated by providing a bioreactor having a growth chamber wherein the cells are grown between a multitubular array comprising at least three functionally separate, inert non-degradable and structurally strong tubes or sets of tubes. A constant nutrient gradient is maintained along the entire length of the tubes by perfusing medium through the tubes at a flow rate which is sufficient to expose all areas of the chamber to fresh medium by convective forces rather than diffusion. Oxygen transfer and removal of toxic wastes is improved by the invention herein. In a preferred embodiment, porous inert expanded Teflon tubes are employed having an inner diameter of approximately between 1 and 2 millimeters.

14 Claims, 5 Drawing Sheets

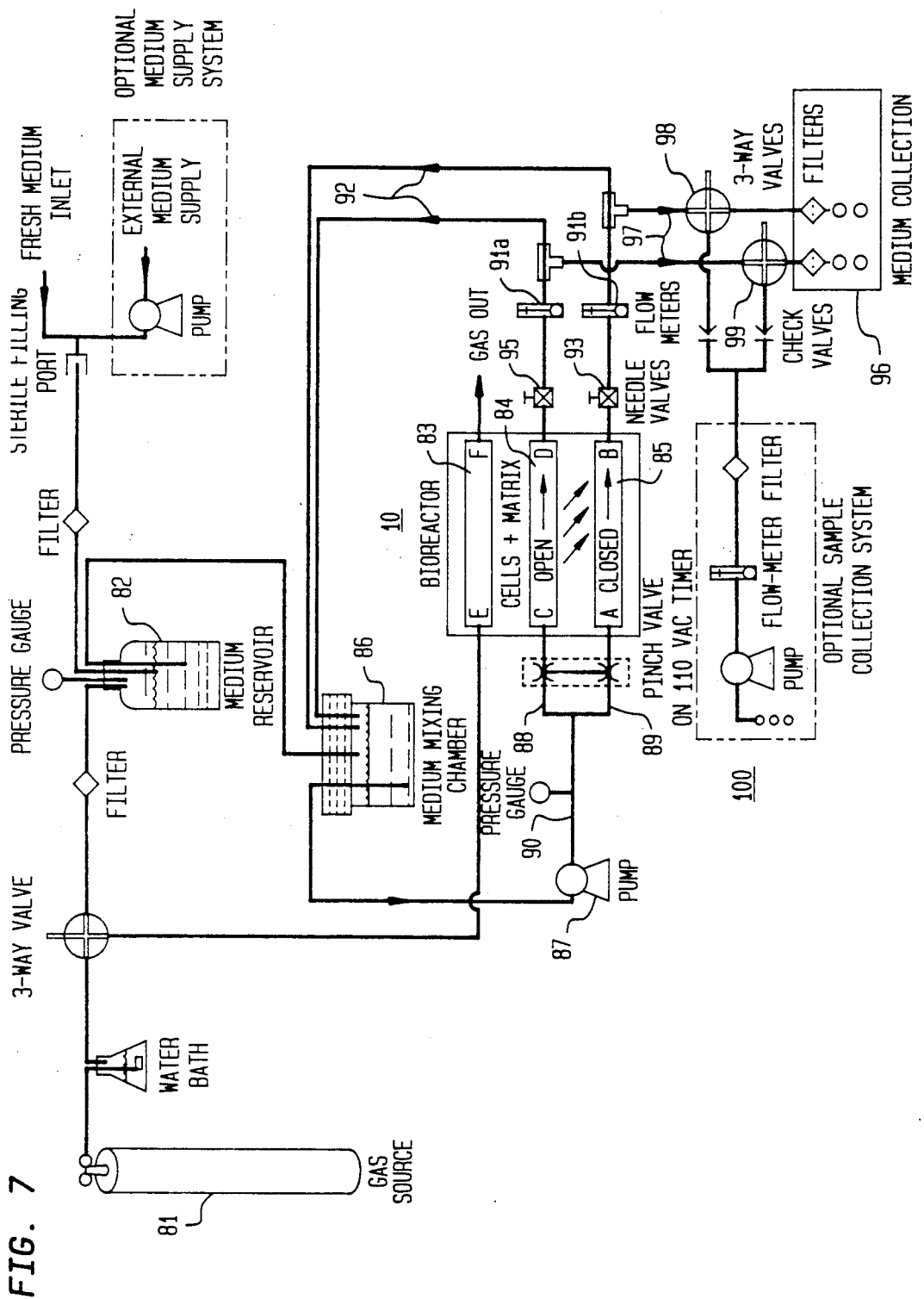

BIOREACTOR SYSTEM

This application is a continuation of application Ser. No. 182,715, filed Apr. 18, 1988, now abandoned.

BACKGROUND OF THE PRIOR ART

This invention relates to bioreactors for mass culture of mammalian cells, and more particularly to a bioreactor system having a multitubular array which simulates in vivo capillary bed conditions wherein anchorage-dependent and anchorage-independent mammalian cells can be cultured.

New technologies for creating biologically active molecules, including monoclonal antibodies, have created a vigorous biotechnology industry. While new methods for introducing genes into cells to make desired biomolecules are being announced on a weekly basis, the problems of producing the biomolecules on a mass scale have not been solved. Existing microbial fermentation systems are often of little use in producing many of the currently desired biomolecules largely because bacteria produce proteins which are different from those of mammalian cells. As a consequence, mammalian cell growth is becoming a very important area in the production of pharmaceutical products. Unfortunately, all currently available bioreactors used for growth of mammalian cells suffer from one or more of the following problems: inadequacy of oxygen transfer, accumulation of toxic wastes, inability to be scaled up, and difficulty in automation.

In vivo production of monoclonal antibodies, for example, involves the intraperitoneal inoculation of mice with antibody-producing hybridoma cells followed by collection of ascites which are fluid-rich in antibodies. However, one mouse often takes up to 8 weeks to produce 40-200 mg antibody and the recovered antibodies are contaminated with mouse proteins that can cause serum sickness when injected into humans. Moreover, mice are expensive to maintain and the cost of production does not decrease with scale-up. Additionally, human monoclonal antibodies cannot be cultured in mice.

In view of the above-stated disadvantages, in vitro culturing techniques, which generally are categorized as either batch or continuous systems, are preferred. However, cell densities in vitro usually do not exceed $1 \times 10^7$ cells/ml and the resulting concentrations of product are also low (0.01-0.1 mg/ml vs. 1-10 mg/ml in vivo).

Batch culture involves growth in a batch of medium with no attempt to separate medium and product from cells continuously. A major problem with batch culture systems is poor oxygen transfer. Mammalian cell oxygen demand ranges between 0.053 mmole $O_2$/L-hr-$10^6$ cells/ml to 0.59 mmole $O_2$/L-hr-$10^6$ cells/ml. Unlike microbial fermentations, bubbles of oxygen cannot be forced through the reactor since mammalian cells lack rigid cell walls and often cannot withstand the resulting shear forces. Several suggested approaches for aerating the cells, such as use of airlift convection forces and restricted impeller techniques, have been employed. However, these approaches only reduce the shear forces and physical trauma to the cells, but do not eliminate these problems. Nevertheless, cell yield is still limited by oxygen concentration. A further significant problem is that of waste elimination. Centrifugation can be used to remove old medium, but this increases the probability of contamination and can also result in substantial cell damage.

Encapsulation of cells either in an alginate gel or in alginate gel surrounded by a semipermeable polymer membrane with controlled pores is another method for cultivating mammalian cells. In the former procedure, cellular proteins pass into the medium while in the latter method the product is trapped in the bead, which then has to be ruptured to release the product. While this can give high concentrations of antibody, both approaches are limited since cells ultimately rupture the beads and are subject to the limitations of all batch processes.

Continuous culture involves separation of cells from medium on a continuous basis. Several approaches include chemostat cell-retention and cell protecting systems (e.g., hollow fibers, ceramic cartridges). The major advantages of continuous culture over batch cultures are the ability to control the concentration of key medium components; the ability to remove wastes before toxic build-up occurs; the ability to maintain a cell culture in its growth state for greater periods of time; and the ability to reuse medium and expensive growth factors, serum and other additives.

Cell-retention production benefits from the continuous flow of medium which results in higher cell densities and product yield by removing growth inhibitors and supplying a fresh source of nutrients to the cells. Many cell-retention systems utilize microcarriers to grow anchorage-dependent cells. Examples of microcarriers included Bioglas brand hollow glass microspheres (SoloHill, Ann Arbor, Mich.); and charged or collagen-coated microspheres, such as Cytodex brand microcarriers (Pharmacia Fine Chemicals AB). In addition to providing a large surface for attachment, the microcarriers can facilitate suspension and separation. These advantages notwithstanding, the use of microcarriers does not alleviate the aforementioned problem of inadequate oxygen delivery absent vigorous agitation or sparging with gas. As discussed hereinabove, this will generally cause severe cell damage due to the shear forces generated.

Another approach which has been explored extensively in this field is the hollow fiber reactor system wherein medium is perfused through hollow capillary tubes to expose the cells to a more natural environment. Cells can be supported by a constant flow of fresh medium and gases and the products can be removed online. One disadvantage with this approach is that the cells grow around and between the capillary tubes and eventually break the fibers. Therefore, this known system cannot be operated for long growth periods, and the cultured cells are difficult to remove.

Another serious disadvantage of hollow fiber reactors is that deleterious metabolic and nutrient gradients develop both axially and radially along the length of the capillary tubes due to the fact that the medium is required to flow quite slowly through the tubes which have narrow inner diameters. Oxygen and carbon dioxide tensions, which are limited by solubility, are maximal at opposite ends of the tubes. The distribution of nutrients, as a result of the slow flow of medium, is effected by diffusion in the hollow fiber reactors. Thus, cells located at different regions in the reactor are subjected to radically different conditions.

It is, therefore, an object of this invention to provide a bioreactor system for mass scale in vitro production of anchorage-dependent and anchorage-independent mammalian cells.

It is also an object of this invention to provide a bioreactor system which will mimic in vivo capillary bed conditions.

It is a further object of the invention to provide a bioreactor system wherein there is independent control of gas concentrations, medium delivery and product removal.

It is an additional object of the invention to provide a bioreactor system wherein cell growth is not limited by oxygen delivery or waste product build-up.

It is still another object of the invention to provide a bioreactor system wherein extensive gas delivery throughout permits advantageous use of lower oxygen concentrations.

It is yet another object of the invention to provide a bioreactor system wherein the problems of shear forces in the growth chamber for oxygenating the cells is obviated.

It is yet an additional object of the invention to provide a bioreactor system wherein negligible pressure and concentration gradients develop along the length of the bioreactor.

It is still an additional object of the invention to provide a bioreactor system wherein movement of nutrients and cell product solutes is achieved by convective flow rather than purely by diffusion.

It is yet a further object of the invention to provide a bioreactor system wherein a multitubular array is resistant to cell-mediated breakdown of the tubes due to excess growth.

It is an additional object of the invention to provide a bioreactor system wherein the individual components can be sterilized, such as by autoclaving.

It is yet an additional object of the invention to provide a bioreactor system which is easy to construct at a relatively low cost and inexpensive to operate.

It is still a further object of the invention to provide a bioreactor system which provides oscillatory flow to ensure that nutrient delivery will be consistent throughout the reactor even at high cell concentrations.

It is yet a further object of the invention to provide a bioreactor system having micro-mixing in the chamber that is similar to a stirred tank reactor, without the deleterious effects of agitation.

It is a further object of the invention to provide a bioreactor system which provides the advantages of a hollow fiber system without the deleterious development of axial and radial gradients.

It is a still further object of the invention to provide a bioreactor system having the capability of permitting sampling of the cell suspension during a production run.

SUMMARY OF THE INVENTION

The foregoing and other objects are achieved by this invention which provides, in an apparatus aspect thereof, a system for maintaining and culturing cells in vitro. In accordance with an illustrative embodiment of the invention, the system is provided with a first permeable tube which propagates a liquid medium and a second permeable tube which propagates a product fluid. In a specific embodiment of the invention, the first and second permeable tubes are wound about a spool. The spool may be configured to engage with an enclosure which provides a fluid-tight interior volume for enclosing the first and second permeable tubes wound on the spool.

In a highly advantageous embodiment of the invention, there is provided a third permeable tube for propagating a gas having a predetermined composition. The third tube may be formed of an expanded Teflon or a silicone rubber, having a porosity which permits the gas to be transferred readily therethrough. However, in embodiments where the third permeable tube is not provided, a desired gas can be introduced into the culture chamber by equilibration with the medium prior to its being delivered to the culture chamber.

In one embodiment, in order to achieve advantageous minimization of the intertubular distances, the first, second, and third permeable tubes are braided or intertwined with one another prior to being wound on the spool. This ensures that, in embodiments where the first and second permeable tubes have an internal diameter of approximately between 1 and 2 millimeters, the intertubular distance generally will not exceed 2 millimeters. Thus, there is not present in the volume immediately exterior of the permeable tubes a point where a cultured cell may be located which is further than approximately 2 millimeters from any of the three types of permeable tubes. In an alternative embodiment, the tubes are randomly coiled in the reactor, to ensure that there is an even distribution of nutrients and gas throughout the reactor.

The first and second permeable tubes are preferably formed of a microporous polyfluorinated hydrocarbon material. Such material is commercially available from W. L. Gore & Associates, Inc. (Elkton, Md.), under the trademark Gore-Tex or from other sources such as Impra Technologies, Tempe, Ariz. This material is preferably provided with pores therein having a pore diameter of approximately between 2 and 4 microns, with an overall porosity of approximately 70%. In addition, the material is advantageously inert to all common chemicals, is resistant to temperatures from $-450$ degrees F. to $+550$ degrees F., is naturally hydrophobic, allows gases to flow easily through the walls, and is non-toxic to the cells. In tubing form, burst pressures greater than 140 psi can be achieved with this material. As a consequence of these properties, the tubing normally repels water but can transfer hydrophilic (aqueous) materials, such as culture medium, if the fluid pressure exceeds 1 atmosphere or if the tubing is wetted with a surfactant prior to use. Moreover, the pores are large enough to permit a convective flow between the first and second permeable tubes.

In a specific illustrative embodiment, the polyfluorinated hydrocarbon (Teflon) tubing has a pore size of 3.5 $\mu$m, an inner diameter of 1.0 mm, an outer diameter of 1.8 mm, and an overall porosity of 70%.

In certain embodiments, the second permeable tube which propagates the product fluid is closed at one end thereof. In this manner, this tube withdraws used medium or product, which may include waste, through its walls. In other embodiments, however, the second permeable tube may be used to provide reversible delivery of components. Such reversibility can be achieved over a wide range of pressure amplitudes and frequencies.

The present invention is useful for the production of a wide variety of cells and other organisms. These include: monoclonal antibodies, viral vaccines, and hormones. The system of the present invention can also be used for biologicals and drugs, such as lymphokines, which are useful in treating, curing, and preventing various viral or malignant diseases and immune disorders, enzymes, tumor-specific antigens, viral insecticides, etc. In addition, non-mammalian cell lines can be cultured, such as certain bacteria and fungi under conditions for fermentation, as long as the pores of the tubes employed in the system are small enough to prevent passage therethrough of the microorganisms.

In accordance with a method aspect of the invention, a liquid medium is supplied to a cell culture chamber via a medium supply tube formed of a microporous inert material having pores therein which are smaller than the cells being cultured. The liquid medium is supplied at a flow rate which is sufficient to preclude diffusion of a component of the liquid medium in a single pass of the liquid medium through the medium supply tube. Further in accordance with the method, a product is withdrawn from the cell culture chamber via one or both tubes which are formed of a microporous material having pores therein which are smaller than the cells being cultured.

In a highly advantageous embodiment, a pressure differential is maintained between the medium supply tube and the product tube. This pressure differential produces a convection current between these two tubes. In certain embodiments, the pressure differential may be characterized by a pulsing amplitude.

The method invention further includes the step of supplying a gas to the culture cell. In one embodiment, the gas is equilibrated with the liquid medium prior to its being supplied to the culture cell. However, in other embodiments, the gas may be provided via a gas supply tube which is formed of an inert polymeric material having pores therein of a size which permit transference of a gas therethrough to the surrounding liquid medium. In a specific illustrative embodiment, the gas supply tube is a thin-walled silicone rubber tube.

In the practice of the invention, laminar flow for the medium is maintained at a rate of approximately 2,000 ml/hr through a culture cell chamber having a capacity of 5 liters. The flow rate of the medium can be changed by adjusting the speed of a peristaltic pump, or by changing the diameter of the tubes therein. The rate of gas flow can be adjusted with valves and regulators. The flow rates which are possible in the practice of the invention are quite rapid in comparison to known systems, such that the rate limiting factor is the cellular uptake. Mass transfer within the chamber is achieved by means of convection flow, rather than diffusion. Additionally, pressure gradients established within the chamber permit the individual cells, in certain embodiments, to situate themselves at optimized locations where essentially full cellular contact is achieved, thereby shifting the cells from proliferation to maximal function.

BRIEF DESCRIPTION OF THE DRAWING

Comprehension of the invention is facilitated by reading the following detailed description in conjunction with the annexed drawing, in which:

FIG. 7 is a schematic diagram which shows an alternative mode of operating the bioreactor system of the present invention.

DETAILED DESCRIPTION

Figure 1:
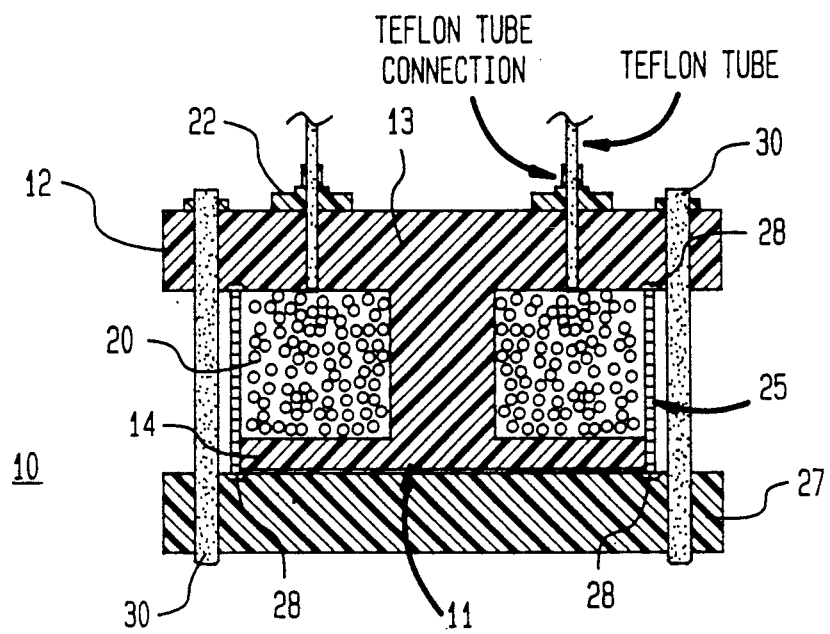
FIG. 1 is a cross-sectional representation of a culture cell chamber constructed in accordance with the principles of the invention.

FIG. 1 is a cross-sectional representation (taken across line 2—2 of FIG. 2) of a specific illustrative embodiment of a culture cell chamber 10 constructed in accordance with the present invention. The culture cell chamber is formed of a spool 11 having a top portion 12, a core portion 13, and a bottom portion 14. In this embodiment of the invention, three flexible, permeable tubes 20, are braided with one another and wound on core portion 13 of spool 11. The braided and wound permeable tubes are held on the spool by the top and bottom portions thereof. In the specific illustrative embodiment shown in this figure, each such permeable tube is connected by at least one end thereof to a respective one of connector members 22 via a silicone tube junction. Such connector members permit fluid communication between the ends of the permeable tubes and the exterior of the culture cell chamber, as will be described hereinbelow.

The culture cell chamber of FIG. 1 is closed to form a fluid-tight enclosure, in this embodiment, by a substantially annular glass wall 25 which is in sealing communication with the underside of top portion 12 of spool 11, and a base member 27. Such sealing communication is effected by a pair of seals 28 which may be formed of a polyfluorinated material, such as Teflon or rubber O-rings. The fluid-tight seal is completed by application of a sealing force by actuation of a plurality of bolts 30.

In another embodiment (not shown), this reactor of the present invention is not provided with a spool, and instead the tubing is interwoven amongst a mesh (e.g., a mesh of glass wool, polypropylene, stainless steel, or the like). In yet another embodiment (not shown), the reactor again is not provided with a spool, and the tubing is randomly, or otherwise, coiled compactly within the reactor such that the intertubular distances are no greater than 2 mm.

In a highly advantageous specific illustrative embodiment of the invention, the multitubular array, as indicated, is formed of three functionally separate, inert non-degradable and structurally strong tubes, or sets of tubes. Preferably, a constant nutrient gradient is maintained along the entire length of the tubes by perfusing medium through the tubes at a flow rate which is sufficient to expose all areas of the chamber to fresh medium by convective forces rather than diffusion. The convective forces greatly improve oxygen transfer and the removal of toxic wastes. In a practical embodiment, porous inert expanded Teflon tubes are employed having an inner diameter of approximately between 1 and 2 millimeters.

Figure 2:
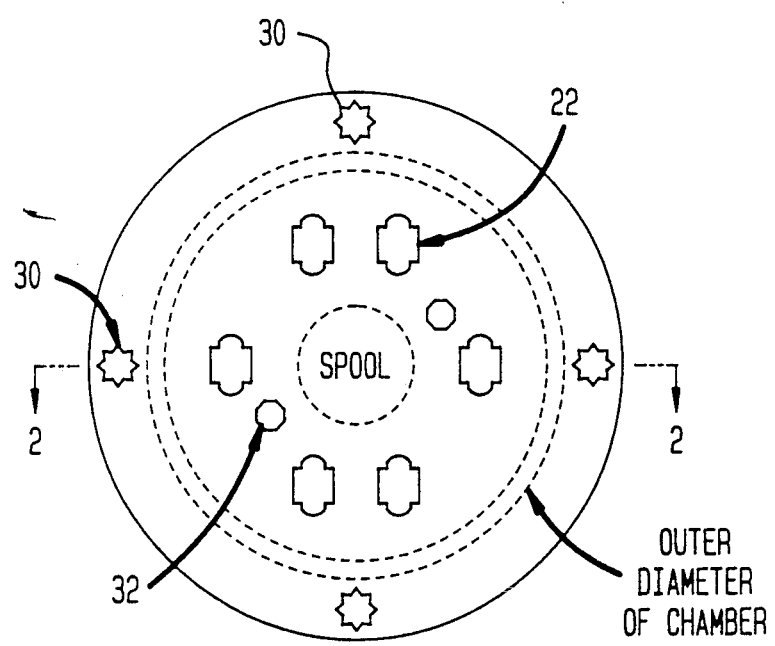
FIG. 2 is a top plan view of the embodiment of FIG. 1.

FIG. 2 is a top plan view of the embodiment of FIG. 1 and shows the substantially cylindrical configuration of the specific illustrative embodiment. As shown, this embodiment is provided with four bolts 30 which effect the sealing force. In addition, this embodiment is provided with six connector members 22, as described hereinabove with rubber O-rings provided underneath as a seal. In addition, this figure shows a plurality of sampling ports 32. Such sampling ports may be in the form of silicone rubber diaphragms which permit passage therethrough of a conventional hypodermic needle to extract fluid from within the culture cell chamber.

Figure 3:
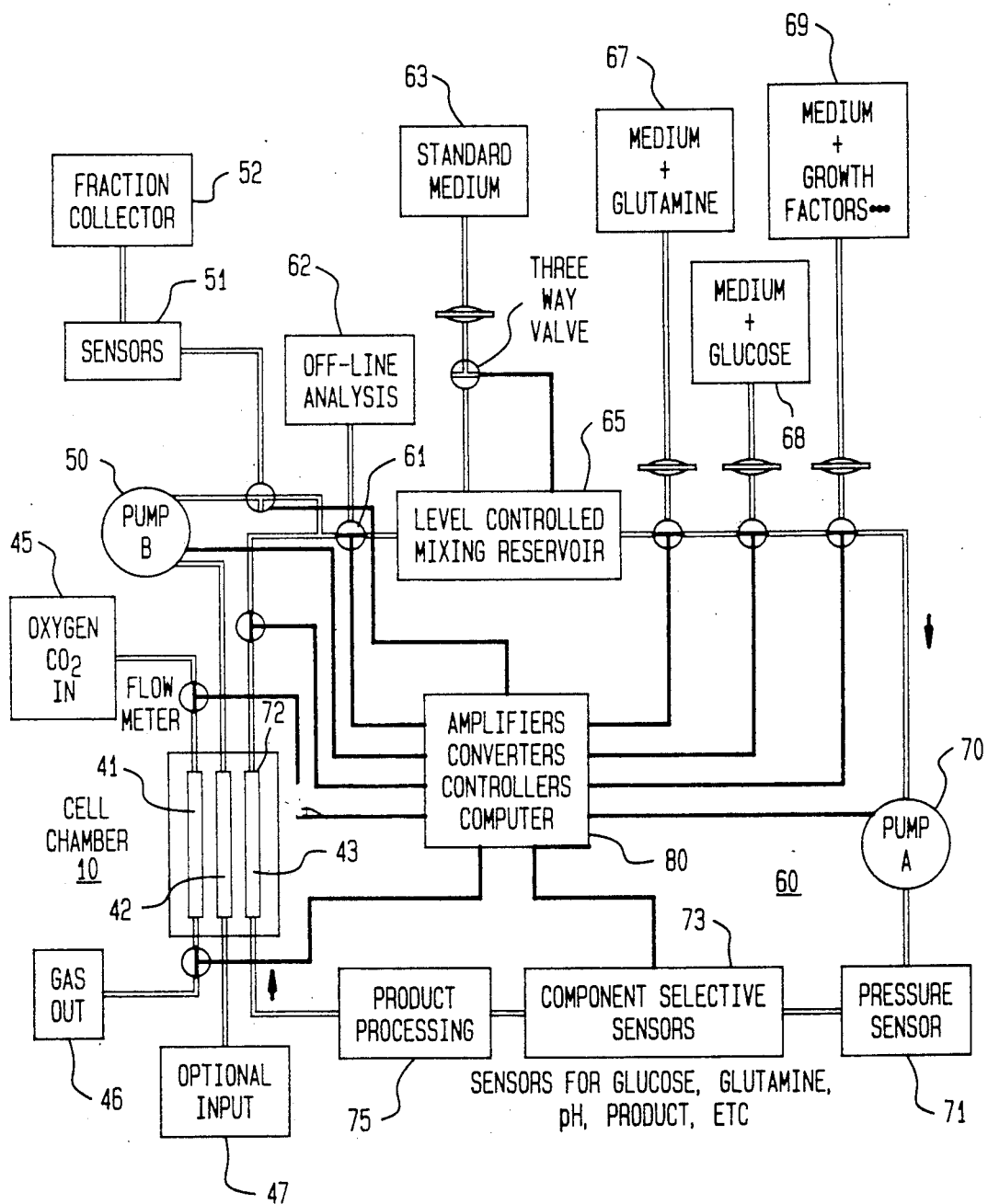
FIG. 3 is a schematic diagram which shows an illustrative mode of operating the bioreactor system of the present invention.

FIG. 3 is a schematic representation of a system which illustrates one mode in which the culture cell chamber of the present can be operated. Culture cell chamber 10 is illustrated schematically and shown to have three permeable tubes, 41, 42, and 43 disposed therein. It is to be understood that the permeable tubes are presented only schematically herein, and each tube thus illustrated may represent a plurality, or set, of similarly functioning tubes. Permeable tube 41 is a gas supply tube which is shown to be connected to a gas supply 45. Gas supply 45 is shown to provide oxygen and carbon dioxide in this embodiment. An illustrative gas mixture may include carbon dioxide (5%), oxygen (10%), and nitrogen (85%). In addition, a gas disposal outlet 46 is shown.

Permeable tube 42 is a product tube which operates to remove medium from the culture cell chamber. Additionally, in this embodiment, permeable tube 42 can be used to provide a desired component, from optional input 47. Also in this embodiment, the material removed via permeable tube 42 can be recirculated such as by a pump 50 to the medium supply, as will be described herein. The recirculated material obtained from permeable tube 42 can be monitored by sensors 51 and collected, for analysis such as by a fraction collector 52.

Permeable tube 43 is a medium supply tube which supplies fresh medium, as well as other components to the culture cell chamber. This permeable tube is connected at both ends thereof to a loop 60 which controls the composition and pressure of the medium, as well as permits analysis and processing.

Loop 60 begins at the top end 72 of permeable tube 43 and is provided with a port 61 which permits the fluid removed from culture cell chamber 10 to be analyzed off-line at station 62. Medium supplied from medium supply 63 is delivered via a plurality of valves to a level-control mixing reservoir 65 which is in the loop. The medium therein is conducted through the loop where various other fluid components can be added thereto. These include, for example, glutamine from a supply 67, glucose from a supply 68, and various growth factors from a supply 69.

Propagation of the fluid through the loop is motivated by a pump 70 which is controlled by a pressure sensor 71. The pressurized fluid is then subjected to a plurality of sensors, which are schematically illustrated in this figure by a sensor bank 73. The sensors in the sensor bank may include sensors for glucose, glutamine, pH, product, oxygen, and any other desired component. In this embodiment, the product can be processed at a processing station 75. This station is interposed in the loop between the sensor bank and permeable tube 43.

In operation, pressure gradients can be established to permit bulk flow from permeable tube 43 to permeable tube 42, or from permeable tube 42 to permeable tube 43. Such pressure gradients enable delivery of medium components by convection instead of, or in addition to, diffusion. Pump 70 can be controlled so as to provide optionally reversible delivery of components, in pulses over a wide range of amplitudes and frequencies.

In other embodiments of the invention, the fluid which is propagated through permeable tube 41 need not be a gas. Instead, such fluid may be a gas-exchanging liquid such as artificial blood. It may be desirable in certain embodiments, to equilibrate gas with the medium, prior to its being introduced into the culture cell chamber. In addition, in embodiments where a gas is provided, the gas may be in the form of bubbles mixed with the recirculating medium. Such bubbles segment the medium and are removed after the medium exits from the culture cell chamber.

The system illustrated in FIG. 3 can easily be automated. Such automation is schematically illustrated as a control system in an apparatus block 80 which is indicated as containing amplifiers, converters, controllers, and a computer. As shown, the control system communicates with sensor bank 73, a plurality of flow control and flow monitoring devices, as well as a plurality of control valves.

Figure 4:
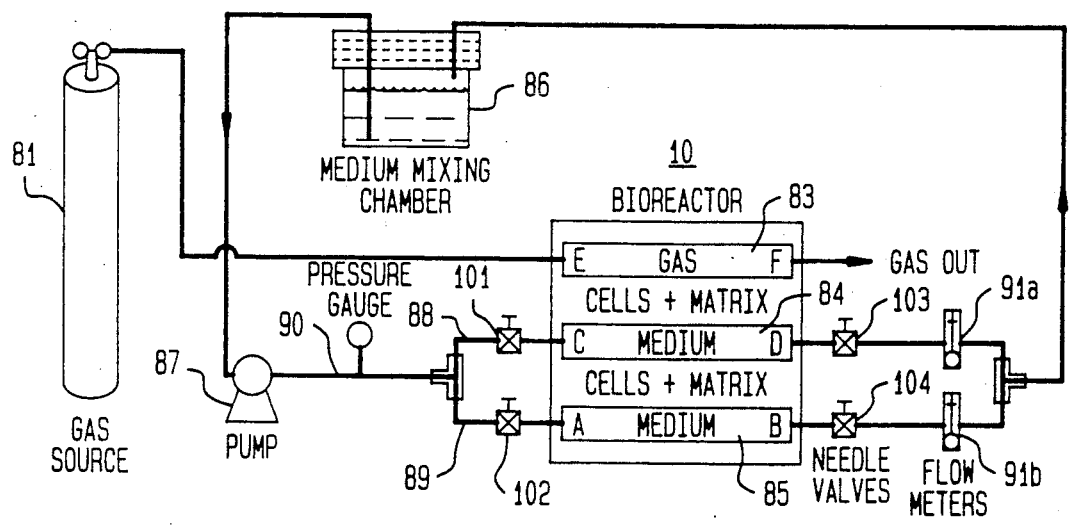
FIG. 4 is a schematic diagram which is helpful in illustrating alternative modes of operating the bioreactor system of the present invention.

In order to understand more readily the advantageous modes of operation of the bioreactor system of the present invention reference is made to the schematic representation of FIG. 4. In this figure, elements of structure bearing analogous correspondence to the elements of structure in the previous drawing figures are similarly designated.

FIG. 4 illustrates a bioreactor system constructed and operated in accordance with the principles of the present invention. Filtered gas from a source 81 is provided under pressure, saturated with water, and then passed through gas permeable silicone tubing 83 inside bioreactor 10. Medium is provided from a reservoir, or a medium mixing chamber 86, transferred by operation of a peristaltic pump 87 via a main medium line 90 where the medium flow is divided and directed selectably to one or both of two microporous medium lines 88 and 89.

After passing through bioreactor 10, the medium is conducted through a flow meter 91a and/or 91b and is either recycled back into medium mixing chamber 86. Alternatively, the medium can be collected in a collection container (not shown).

Valves 101 through 104 control the mode of operation of the bioreactor system of FIG. 4. In a transtubular mode, i.e., where the flow is provided by a pressure differential between lines 88 and 89, valves 102 and 103 are closed and valves 101 and 104 are open. Medium enters through tubing 84 and exits through tubing 85 by convective flow. The flow in the reactor can be reversed by closing valves 101 and 104 and opening valves 102 and 103 so that medium flows into tubing 85 and exits through 84. Such reversal of the direction of transtubular flow permits cells which are being cultured in the intertubular interstices, to have proximity and access to the medium supply from either direction. In this manner, the productivity of the tubular interstitial region is enhanced.

In an alternative mode of operation, medium circulation can be effected from only one of the lines. By way of example, valves 101 and 103 are closed and valves 102 and 104 are open so that the medium flows through tubing 85, and not through tubing 84. Product and/or waste can be drained at least periodically through tubing 84. Valve 104 can be closed and opened periodically to facilitate product removal. Of course, this mode of operation can be reversed in its entirety whereby medium flow is effected exclusively through tubing 84.

Figure 5:
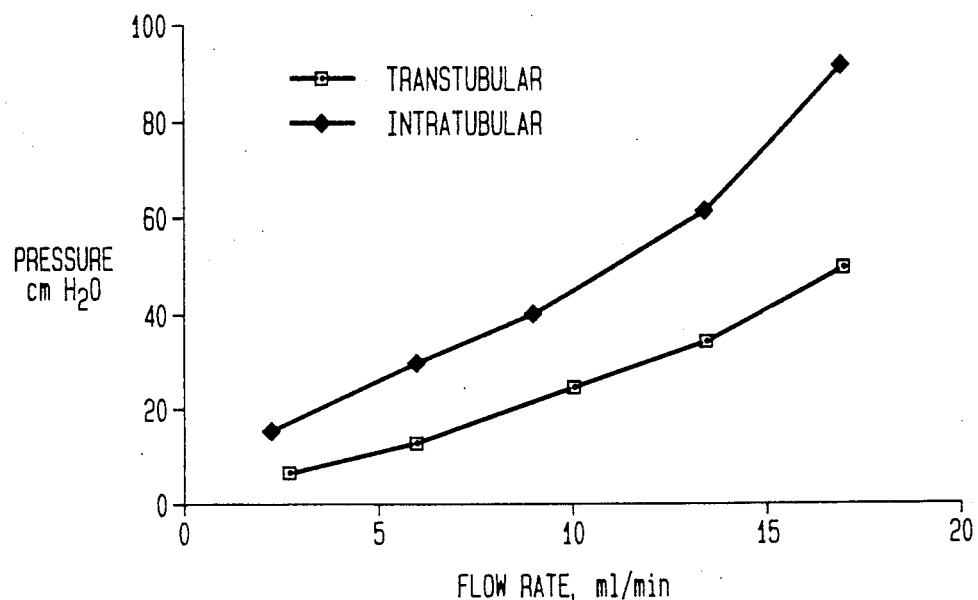
FIG. 5 is a graphical representation which illustrates the relationship between transtubular and intratubular flow rates versus pressure in one mode of operation of the system of FIG. 4.

FIG. 5 is a graphical plot illustrating the total flow rate versus pressure in the system of FIG. 4 for the particular mode of operation where valves 101, 103, and 104 are open and valve 102 is closed. The data for this plot was obtained by varying the total flow rate in the main line 90 and measuring the flow rate from tubing 84 and 85 at flow meters 91a and 91b, respectively. As is evident from this figure, an increase in the flow rate causes a corresponding increase the pressure in both lines so that undesirably high pressure gradients, which might damage the cells, do not develop. However, there is sufficient pressure differential between the lines to achieve the desired convective flow.

Figure 6:
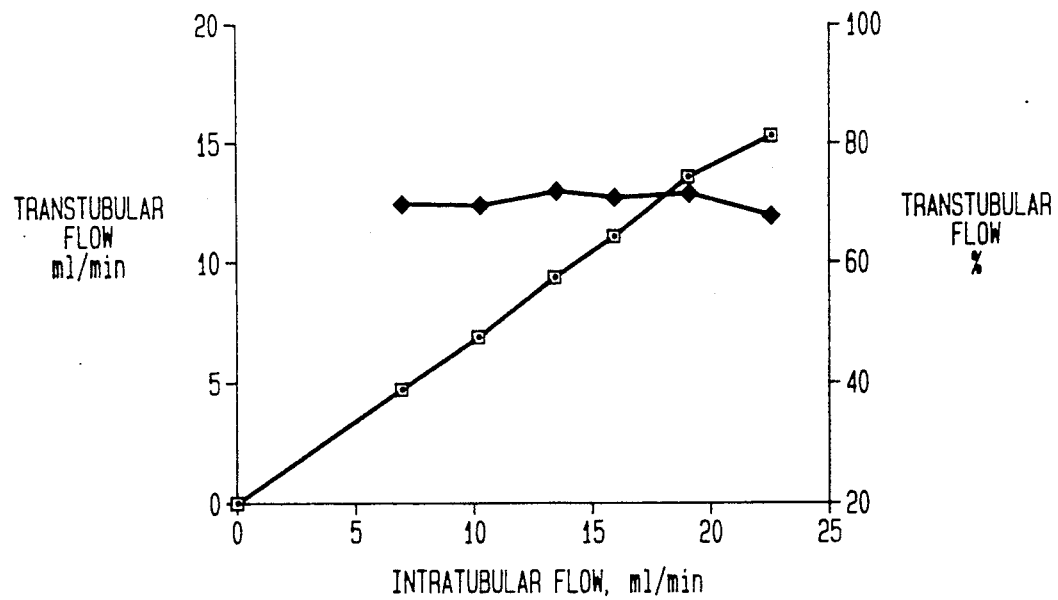
FIG. 6 is a graphical representation illustrating a surprising relationship between intratubular and transtubular flow rates in a specific embodiment of the invention.

FIG. 6 is a graphical plot which illustrates the relationship between total flow rate, intratubular flow through tubing 84 and transtubular flow rate through tubing 85. Percent transtubular flow is defined as the percent ratio of the convectivity generated transtubular flow to the main intratubular flow. As intratubular flow increases, transtubular flow increases in a linear fashion. However, the percent transtubular flow remains relatively constant around 70%.

FIG. 7 is a schematic representation which shows the system of the present invention operating in an oscillatory mode. Elements of structure which have analogous correspondence to elements referenced herein with respect to other drawing figures are correspondingly designated.

In FIG. 7, filtered gas from source 81 is provided under pressure, saturated with water, and then passed through gas permeable silicone tubing 83 inside bioreactor 10. Medium is provided from a reservoir 82, transferred via a peristaltic pump 87 or by means of gas pressure on the surface of the medium to a medium mixing chamber 86, and then transferred into main medium line 90 where it is further divided into one or both of the two microporous medium lines 88 and 89. After passing through bioreactor 10, the medium passes through a flow meter 91a and/or 91b and is either recycled back into the medium mixing chamber 86 in the direction of arrows 92 (batch-recycle operation) or collected in a medium collection container 96 in the direction illustrated by arrows 97 (net perfusion operation).

In transtubular operation, one end of tubing 85 (transtubular line) is closed at valve 93 and the medium perfuses from the main line through tubing 84, through the extratubular interstices and then enters into tubing 85. This transtubular flow is measured by a flow meter 91b and then the medium goes back into the medium mixing chamber 86 or into the other external container 96. As shown in FIG. 7, a pinch valve 94 which alternatively closes and opens one medium line (e.g., tubing 84) while reciprocally opening and closing another medium line (e.g., tubing 85) can provide oscillatory transtubular flow. Valve 95, provided at the opposite end of tubing 84, and valve 93 can be used to control which medium line is the transtubular line. As previously noted, oscillatory operation of the systems enhances the distribution of medium and nutrients throughout the reactor, resulting in greater productive utilization of the volume therein, particularly the intertubular spaces. Thus, net reactor productivity is improved.

The embodiment of FIG. 7 is provided with an optional sample collection system 100 for sampling the cell suspension during a production run. Medium flowing in the direction illustrated by arrows 97 is diverted at 3-way valves 98 and 99 to sample collection system 100.

For purposes of scaling up the system, the diameters and lengths of the tubing, and the multiplicity of banks of tubes, can be changed over a wide range. In addition, the dimensions of the cell culture chamber can also be varied over a significant range.

As a result of measurements taken of the residence time distributions, it has been determined that the intertubular interstices, where the cells are located, are well mixed solely by convective bulk flow between the porous Teflon tubing (e.g., tubes 84 and 85 in the embodiment of FIG. 5). Therefore, the bioreactor of the present invention provides a uniform environment to the cells and possesses the advantages normally associated with free suspension systems. Through the aforementioned residence time distribution measurements, it has further been determined that the liquid elements in the tube are effectively exposed to the entire volume within the reactor. It is hypothesized that this unique hydrodynamic behavior is achieved as a result of the high porosity of the Teflon tubing. Even with a single tubing (i.e., medium/product removal line), the liquid elements in the tubing can pass the external tubular volume in the reactor and return into the tubing.

Through the determination of the mass transfer coefficients, it has been determined that the oxygen mass transfer coefficient for the bioreactor falls within the range of values that are observed for sparged aeration in other reactors. This value can be achieved with flow rates that are normally run in the reactor and are not detrimental to the cells. Hence, from the residence time distributions and the mass transfer coefficients, the reactor has advantages of both cell-retention and cell-protecting systems, without their disadvantages.

The ability to change tubing lengths, diameters, and multiplicity is a significant advantage since conventional hollow fiber reactors cannot be scaled-up in this manner. In such known systems, the hollow fibers must be kept short, and even then, deleterious metabolic gradients develop along their length. Scale-up of the system of the present invention can also be accomplished by utilizing multiple bioreactors operated in parallel.

A further significant advantage of the present invention relates to the provision of suitable pressure gradients. This causes a portion of the rapidly recirculating medium to flow slowly from the medium tube, past the cells growing in the intertubular space, and into the product tube. This allows waste products, such as lactic acid, to be removed continuously or periodically with the desired products. Gas and nutrient exchanges occur primarily by diffusion between the cells and the closest tubes providing recirculating medium or gas. Thus, the cells are never more than a short distance from the gas and nutrient medium tubes. Although rapid rates of flow in the medium and gas tubes effectively eliminate significant gradients in concentration from one end of each tube to the other, small gradients will exist between the tubes. As indicated, the cells can take advantage of these gradients by situating themselves into areas of optimal concentration of nutrient and gas. This distribution resembles that which occurs in a bed of solid tissue, since the small diffusional distances permit maintenance of full viability. Thus, the system is capable of producing cell densities higher than $5 \times 10^7$ cells/ml.

Anchorage-independent cells can settle without dying from build-up of toxic wastes or inadequate gas and nutrient exchange. In certain embodiments, such cells can be kept in suspension by agitating the reactor, or by increasing the buoyant density of the medium. Additionally, anchorage-dependent cells can be provided with solid matrices for attachment, such as hollow glass microspheres (Bioglas (tm)) or microcarriers (Cytodex (tm)). For anchorage independent cell, provision of a matrix prevents the cells from settling or permits the cells to form a solid tissue.

A bioreactor constructed in accordance with the invention can easily be switched from various operating modes. For example, in a cell growth phase, a batch-recycle mode can be employed. When cell maintenance is desired, the operating mode can be switched to a perfusion mode. The various operating modes can also be employed to create a nutrient environment, surrounding the cells, wherein the delivery of growth factors and hormones is in a dynamic pattern closely resembling in vivo conditions.

In an experimental trial intended to demonstrate feasibility of the growth phase mode, a bioreactor constructed in accordance with the present invention was inoculated with a rat leukemic cell line (L1210) and operated in a batch recycle mode. In a bioreactor having an 80 ml volume, cells grew from an initial cell concentration of $1 \times 10^5$ cells/ml to a final concentration of $5 \times 10^6$ cells/ml in a seven day run with 95% cell viability. In comparison, the same cell line grown in T-flasks and spinner flasks achieved a maximum concentration of about $1 \times 10^5$ cells/ml.

Although the invention has been described in terms of specific embodiments and applications, persons skilled in the art can, in light of this teaching, generate additional embodiments without exceeding the scope or departing from the spirit of the claimed invention. The specific composition of the various elements of the bioreactor system, for example, should not be construed as a limiting factor. In the illustrative embodiments herein, the choice was based on materials which are non-toxic (if in contact with the medium) and which can withstand sterilization by autoclaving. Accordingly, it is to be understood that the drawing and descriptions in this disclosure are proffered to facilitate comprehension of the invention and should not be construed to limit the scope thereof.

What is claimed:

1. An apparatus for maintaining and culturing cells in vitro therein, the apparatus comprising:
    a housing;
    a first permeable tube arranged in said housing for supplying a liquid medium, said first permeable tube being arranged in said housing along a first path therein which has a first predetermined length, said first permeable tube having first and second ports at respective ends thereof and positioned and arranged so as to communicate with the exterior of said housing, said first path being substantially randomly disposed within the housing;
    a second permeable tube arranged in said housing for receiving the liquid medium supplied by said first permeable tube and containing a product produced by the cells, said second permeable tube being arranged in said housing along a second path having a second predetermined length, said second path being maintained throughout said second predetermined length of said second path in close proximity to substantially the entire first predetermined length of said first path by being intertwined therewith so as to provide a varying distance between said first and second paths throughout said first and second predetermined lengths, and having first and second ports at respective ends thereof and positioned and arranged so as to communicate with the exterior of said housing, whereby a convective flow of the liquid medium is maintained in a region in the vicinity of said first and second paths; and
    enclosure means for providing a fluid-tight closure for said housing, said first permeable tube and said second permeable tube being disposed within said fluid-tight closure of said enclosure means.

2. The apparatus of claim 1 wherein there is further provided pulsed-pressure medium supply means for supplying said liquid medium to said first permeable tube.

3. The apparatus of claim 1 wherein at least one of said first and second permeable tubes has an internal diameter of approximately between 1 and 2 millimeters.

4. The apparatus of claim 1 further including spool means for supporting said first and second permeable tubes so as to be substantially randomly disposed within said housing.

5. The apparatus of claim 1 wherein there is further provided a third permeable tube for propagating a gas having a predetermined composition, wherein said third permeable tube is intertwined with said first permeable tube and said second permeable tube.

6. The apparatus of claim 5 wherein said first, second, and third permeable tubes are arranged to be intertwined in a braided manner with one another.

7. The apparatus of claim 5 wherein at least one of said first, second, and third permeable tubes is provided with a nonporous tubing affixed at an end thereof for connecting said one of said first, second, and third permeable tubes to a connector.

8. The apparatus of claim 5 wherein said third permeable tube is formed of a gas-permeable silicone rubber.

9. The apparatus of claim 5 wherein said first, second, and third permeable tubes have an intertubular distance which is less than approximately 2 millimeters.

10. The apparatus of claim 2 wherein said third permeable tube is formed of expanded polyfluorinated hydrocarbon.

11. The apparatus of claim 5 wherein at least one of said first, second, and third permeable tubes is formed of a microporous polyfluorinated hydrocarbon material.

12. The apparatus of claim 11 wherein said microporous polyfluorinated material has an overall porosity of approximately 70%.

13. The apparatus of claim 12 wherein said microporous polyfluorinated material has pores therein having a pore size of approximately between 2.0 and 4.0 microns.

14. An apparatus for maintaining and culturing cells in vitro therein, the apparatus comprising:
    a housing;
    a first permeable tube formed of a microporous polyfluorinated hydrocarbon material having an internal diameter of approximately between 1 and 2 millimeters for supplying a liquid medium;
    a second permeable tube formed of a microporous polyfluorinated hydrocarbon material having an internal diameter of approximately between 1 and 2 millimeters for receiving a product fluid formed at least in part of the liquid medium supplied by said first permeable tube whereby a convective flow of the liquid medium is maintained in a region in the vicinity of said first and second permeable tubes;
    a third permeable tube formed of a microporous polymeric material for conducting a gas-containing fluid having a predetermined composition, said first, second and third permeable tubes being intertwined with respect to one another so as to have a distance therebetween which varies along their respective lengths;

spool means for supporting said first, second, and third permeable tubes so as to be substantially randomly disposed within said housing;

enclosure means for providing a fluid-tight closure for said housing said first, second, and third permeable tubes, and said spool means; and first, second, and third pairs of fluid coupling ports, each such pair of fluid coupling ports being coupled to a respective one of said first, second, and third permeable tubes at respective distal ends thereof, so as to provide fluid communication with the exterior of said enclosure means.

* * * * *